(12) United States Patent  (10) Patent No.: US 7,701,581 B2
Forsell et al.  (45) Date of Patent: Apr. 20, 2010

(54) DEVICE FOR DETERMINING OF PROPERTIES IN A FLUID AND/OR CONSTITUENTS THEREOF

(75) Inventors: Tommy Forsell, Uppsala (SE); Ralf Gutlein, Stockstadt (DE); Johan Rathsmann, Uppsala (SE)

(73) Assignee: DiaSpect Medical AB, Uppsala (SE)

( * ) Notice: Subject to any disclaimer, the term of this patent is extended or adjusted under 35 U.S.C. 154(b) by 366 days.

(21) Appl. No.: 11/887,628

(22) PCT Filed: Mar. 31, 2006

(86) PCT No.: PCT/SE2006/000405

§ 371 (c)(1),
(2), (4) Date: Nov. 26, 2007

(87) PCT Pub. No.: WO2006/104451

PCT Pub. Date: Oct. 5, 2006

(65) Prior Publication Data

US 2009/0079965 A1    Mar. 26, 2009

(30) Foreign Application Priority Data

Apr. 1, 2005  (SE) .................................. 0500778

(51) Int. Cl.
*G01N 21/00* (2006.01)
(52) U.S. Cl. ...................... 356/440; 356/442
(58) Field of Classification Search .................. 356/440, 356/442
See application file for complete search history.

(56) References Cited

U.S. PATENT DOCUMENTS

| 4,113,386 | A | * | 9/1978 | Lepper, Jr. .................. 356/338 |
| 5,430,541 | A | | 7/1995 | Sapp et al. |
| 5,430,542 | A | | 7/1995 | Shepherd |
| 6,090,061 | A | | 7/2000 | Steuer et al. |
| 6,104,491 | A | | 8/2000 | Trainer |
| 6,262,798 | B1 | | 7/2001 | Shepherd et al. |
| 2002/0176068 | A1 | | 11/2002 | Fodgaard |
| 2003/0017079 | A1 | | 1/2003 | Hahn et al. |

FOREIGN PATENT DOCUMENTS

CN    2056251 U    4/1990

OTHER PUBLICATIONS

English translation of Chinese Office Action, dated Mar. 6, 2009 and issued in corresponding Chinese Patent Application No. 200680011372.8.

* cited by examiner

*Primary Examiner*—Roy Punnoose
(74) *Attorney, Agent, or Firm*—Young & Thompson

(57) ABSTRACT

The present invention (HBX) describes a system and device design for measuring and analysis of properties in liquids with suspensions, preferably human body fluids e.g. whole blood and in the fluid existing substances and particles. By penetrating a sample of the liquid suspension with specifically calibrated light passing through a thin well defined layer of the liquid placed in a non added cuvette where the transmitted outgoing light from a measuring area is registered in a spectrophotometer adapted for the specific light and the optic geometrical system arranged for elimination of scattered light. The registered data points in the photometer is then processed in a series of steps for corrections and calculation of the values/results of the desired parameters by use of different algorithms in the microprocessor of the device for final presentation on a display, be stored in a memory and possible communication to other information receiving unit.

19 Claims, 5 Drawing Sheets

Figure 1:
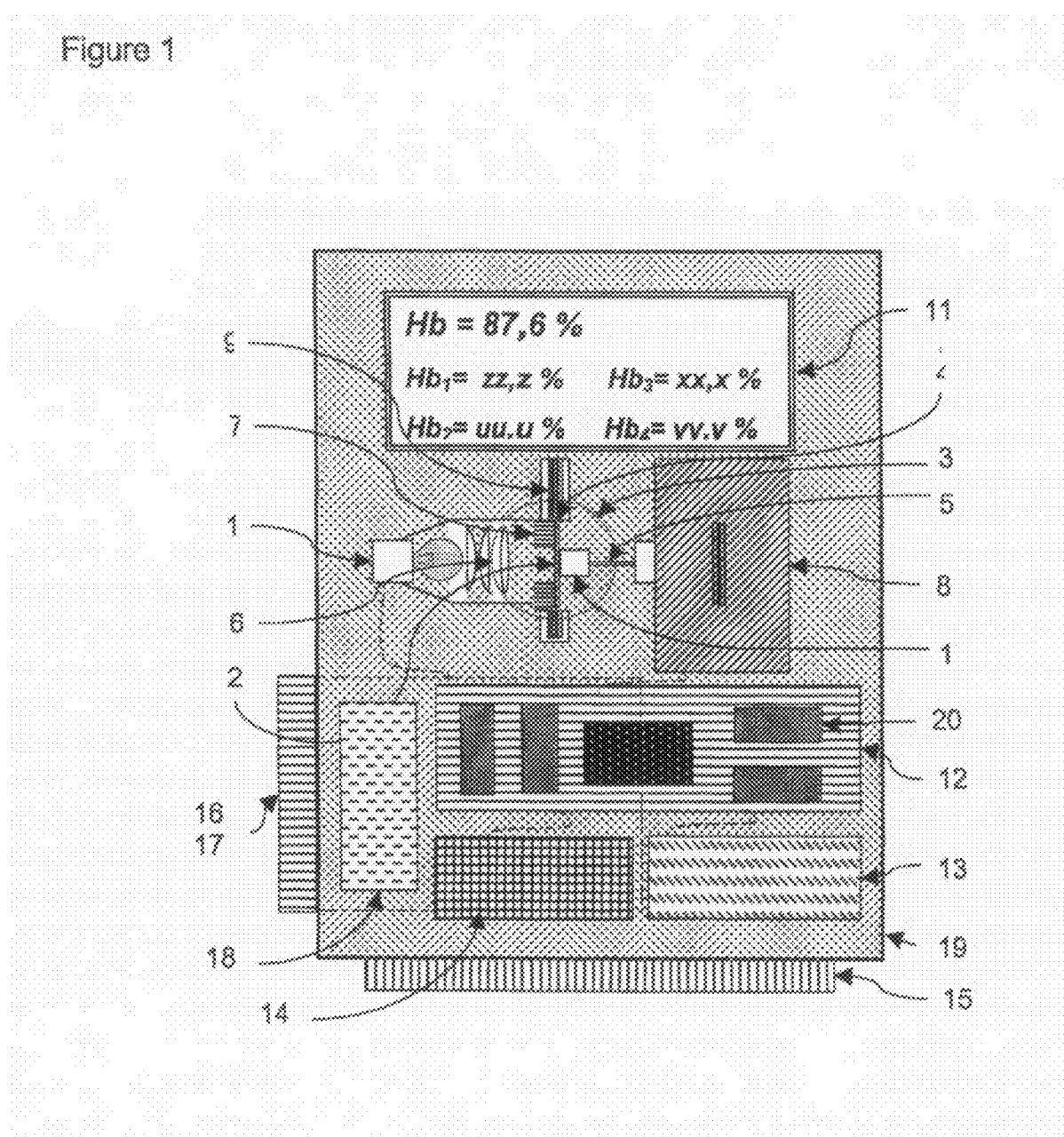

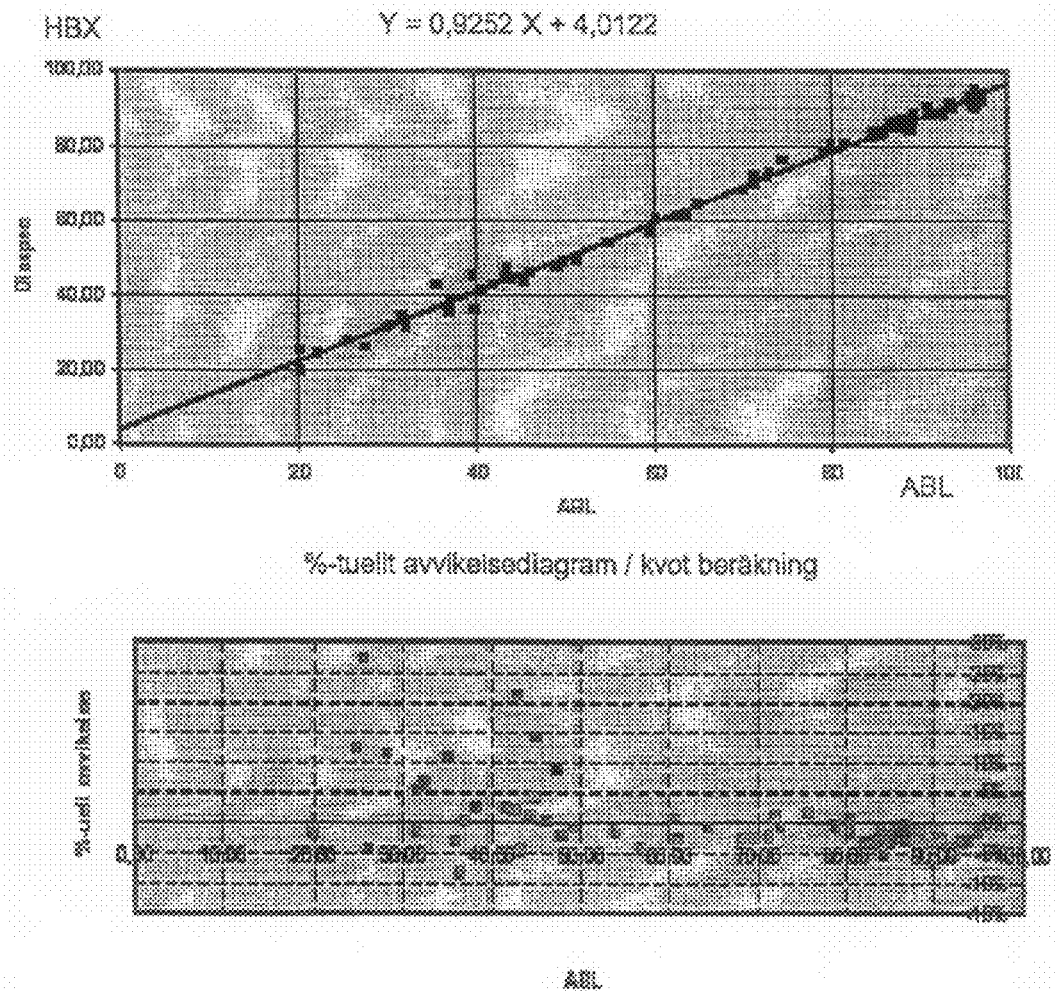
Figure 4  Regression Analysis of HBX relativtive the reference method ABL

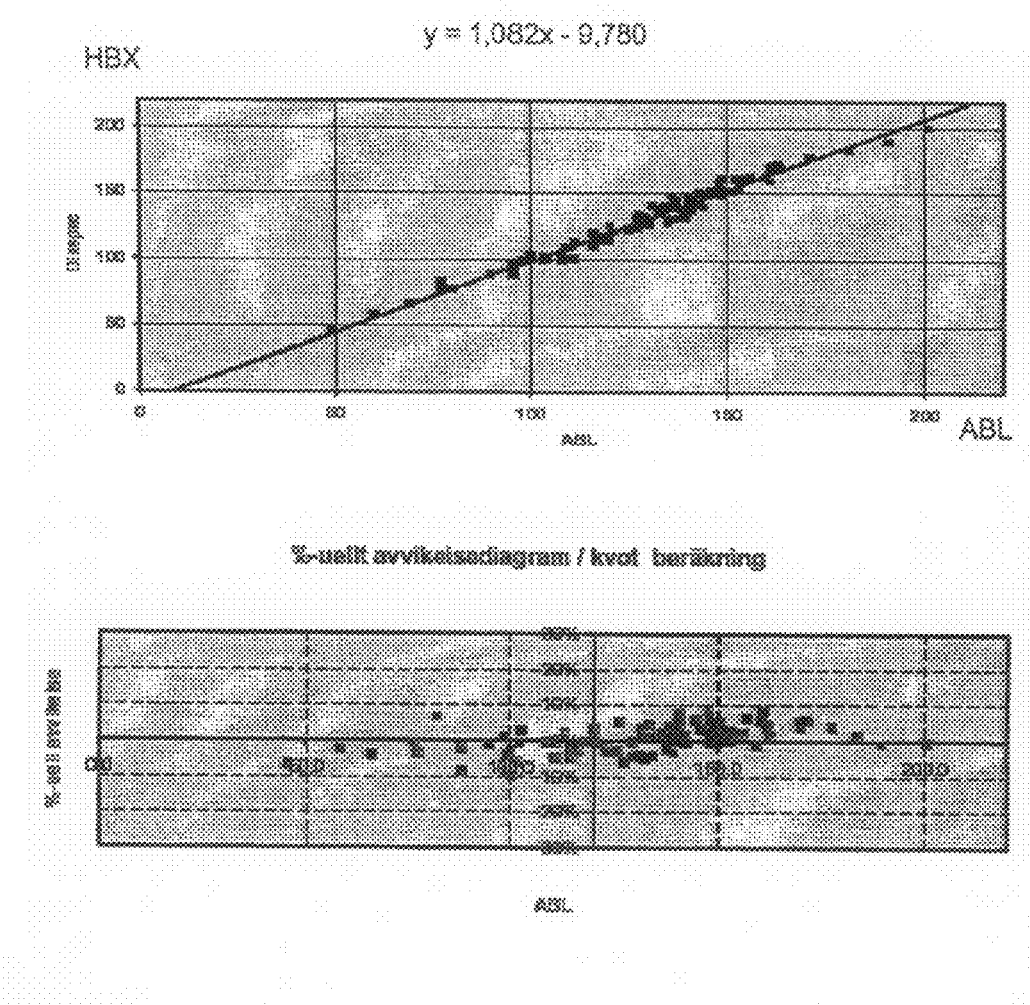

DEVICE FOR DETERMINING OF PROPERTIES IN A FLUID AND/OR CONSTITUENTS THEREOF

BACKGROUND

The invention will occasionally be mentioned in the text as HBX

Spectral analysis is a basic measuring method of properties—chemical or physical as well as others—in a fluid with substances as suspension and/or solution. Spectral photometry of light absorption in chosen ranges of wave lengths is a well established standard method for determination of substances in a fluid and/or the actual condition of the substances at the time of measurement. The method is commonly used within medical technology for the analysis of human blood.

The patent application will in the following be concentrated to and described as the fluid blood, especially human blood for medical purpose, even though the invention is suitable for other body fluids or other organic/non organic fluids with or without substances in suspension, where the technical conditions makes the method applicable.

Blood is commonly described as a complex red fluid consisting of one bright yellow part, plasma, and in the plasma a suspension of blood cells mainly red cells. In an adult the blood volume is approximately 5 litre, of which 40-50% is red cells. The ratio between red cells and plasma is called hematocrit.

Plasma consists of mainly water with proteins, sugar, vitamins, hormones enzymes etcetera. The blood cells are mainly divided in three groups, red cells erythrocytes, with a size significant of 0.007 mm and normally in an amount of 4-5 million/mm$^3$ of whole blood. AN erythrocyte consists of a thin membrane as a kind of balloon in which there is water and a high concentration of the protein haemoglobin (Hb) in various forms, substances that can bind to and release oxygen and carbon dioxide in the circulation.

Normally there is approx. 13-15 g haemoglobin per 100 ml blood in an adult, corresponding to 4-5 million red cell. Even a very small sample of blood taken from one person is a representative amount of blood cells for making measurements to determine certain properties and conditions of the blood.

The haemoglobin value is a measurement of the oxygen transportation capacity of the blood to other tissue and a parameter for patient diagnosis. Haemoglobin value is furthermore a primary safety and quality parameter in blood banking where blood is stored for transfusion purpose and collected as raw material for blood based industrial purposes.

Many other substances e.g. glucose in plasma, is measured by use of photometry as Hb. In general measurement of volumes, activity and condition for substances in blood is a basic diagnostic aid for determination of a persons/patients medical condition.

Haemoglobin (Hb) measurement is one of the most common diagnostic tests in the world today. Billions of tests are performed by use of different methods from the most elementary based on copper sulphate, to complete blood cell counts using sophisticated haematology analysers. These kind of tests are measured on a majority of the world's population one or several times during a life time. Considering the population of the world today of 6 billion and growing, the need for a low cost, yet high quality point of care measurement of Hb and other parameters is very big.

Of all tests performed today a great deal should benefit from being done with higher demand for safety and precision. The limited use of photometric method corresponding to these demands is probably a matter of time and cost. A preferred test method suitable for mass production must be subject to continuous cost reducing product development within the frames of both maintained quality and easiness of use also under rough conditions. Test methods must also fulfil stipulated specifications in standards.

Basically and not including so called non invasive measuring methods related to Hb, the cost of a Hb-test consists of the following factors exclusive the sampling:
- time of measurement
- cost of material/disposables
- equipment, (purchase, handling, service, calibration, lifetime etc.
- In addition to this is the cost for sampling which is basically the same for all capillary methods which is cheaper than venous/arterial blood sampling in tubes.

The major users of single Hb-tests are the Transfusion Centres where the Red Cross is the biggest actor country wise. It is mandatory in most countries to check the Hb-value prior to donation. Another area where it is also mandatory in several countries to check for Hb-value is maternity care.

The best and most common technique for single Hb-measurement is by use of photometry. Normally light with specified wavelength passes through a small chamber (cuvette) containing the specimen. The cuvette can be of different size and shape and are often specially designed. The blood absorbs part of the light and the transmitting light is measured and the Hb-value calculated and displayed in a stable and precise way.

Haemoglobin determination can be made in different ways. Hb-fractions can be measured directly by use of multiple wave lengths or all haemoglobin can be measured indirectly by use of one or two wave lengths after being converted chemically to a stable colour complex e.g. acidmetemoglobin. Common for these methods is that measurement takes place after hemolysation, break down of the red cell membrane, creating a solution of haemoglobin.

It is possible to measure haemoglobin without haemolysing the red cells. This measurement can be done momentarily, which saves time and facilitates the handling, however brings great technical challenges. Whole blood with intact red cells is a colloid suspension with a strong tendency to scatter light, which if not handled in a right way will seriously disturb the measurement. Great consideration must be taken to minimize the scattering effects.

Indirect measurement of total Hb is used In most of the common systems of the less complex kind on the market today. By use of a cuvette that is prepared with reagent for hemolysation and transforming of the haemoglobin to a stable colour complex in typical one minute, thus avoiding the scattering effect but at the same time no specification of the different Hb-fractions. A system utilizing this method successfully has been on the market for more than 20 years and other almost identical systems from Germany and USA have been introduced to the market lately A more complex and sophisticated method is developed and patented in USA. Based on direct measuring of haemoglobin fractions, so called CO-Oximetry in unaltered whole blood. The method is based on multiple wave length measuring of whole blood where the scattering effect is minimized by use of a large sensor in the photometer, collecting also scattered light. Algorithms are used to calculate and distinguish the Hb-fractions. Larger and more expensive disposable cuvettes are used in this system which is in terms of sophistication and price is less suitable for the mass market.

All together the above mentioned and on the market existing systems has good features but also some disadvantages that can be overcome with new technique, new components and new thinking. The disadvantages are relatively high cost per test, time consuming and shelf life of cuvettes with reagent as salt with sensitivity to moisture and thereby risk of incorrect measurements.

Microcuvettes are small cuvettes, size one to a few centimeter square. The cuvette, a type of container for liquids, is placed in an arrangement holding it in place for light penetration and measurement of transmitting light. The cuvette has a specific lumen in shape of a slit where the blood sample is placed and penetrated by light. Substances e.g. Hb-components have specific characteristics regarding light absorption/transmission, deflexion, refraction index etc. These characteristics are known for different Hb-components for example Hb bound to oxygen. Consequently the transmitted light is characterized by the absorption emanating from the substances in the sample together with the reflection and scattering that occurs when light is colliding with particles e.g. cells in during its passage through the sample. It is mainly the absorption that is the information searched in the transmitting light and—in the case of Haemoglobin—is presented in relation to the chosen He-components, for example oxygen saturation.

Each chosen wave length contributes with information and gives additional information about a certain Hb-fraction. Wave length of special interest is absorption max respective min and so called isobestic points. The totally transmitted light consists of a complex and the effect of scattering makes the interpretation of the measurement result even more complex.

GENERAL DESCRIPTION OF THE PRESENT INVENTION

Figure 2:
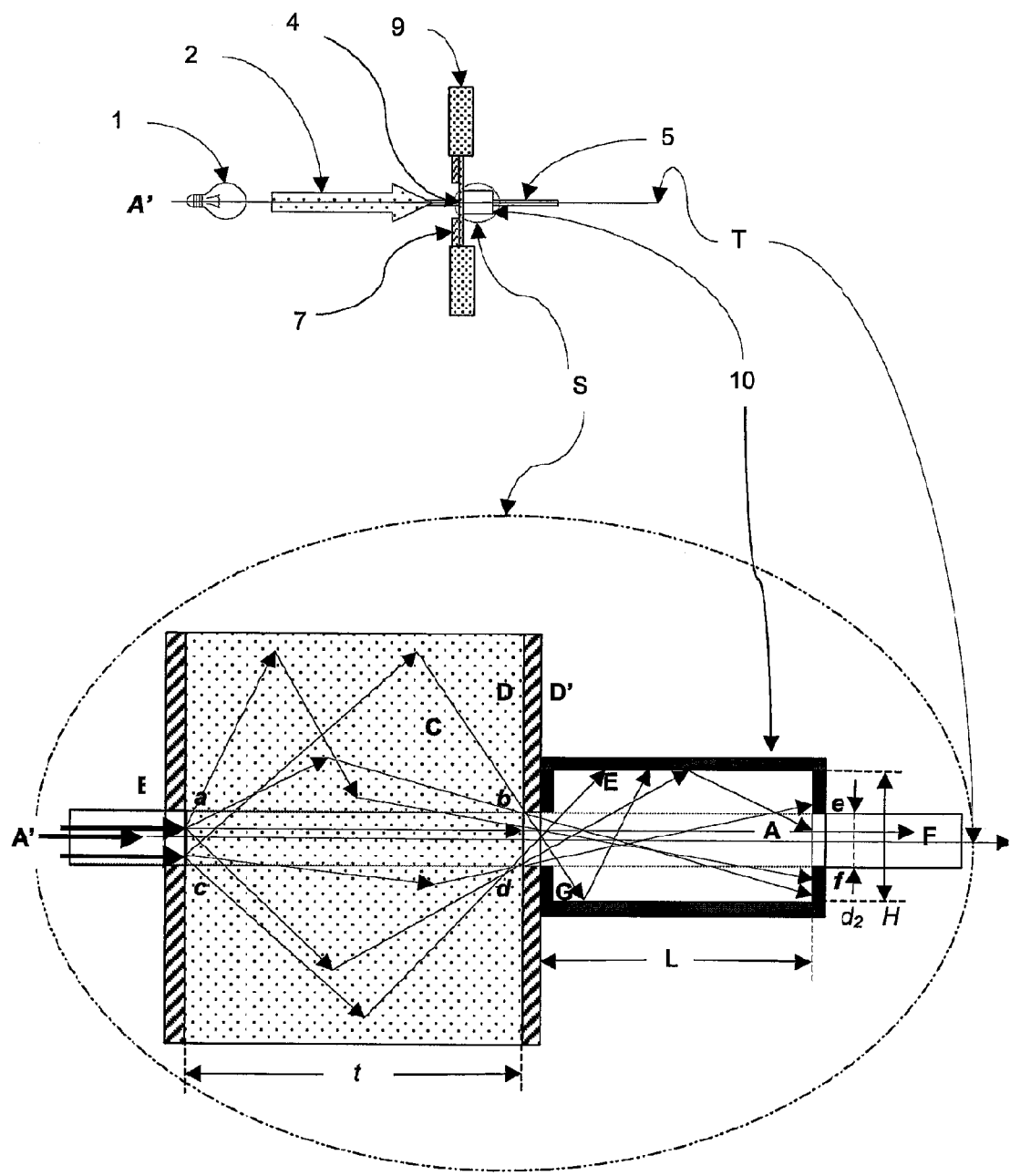
Figure 3:
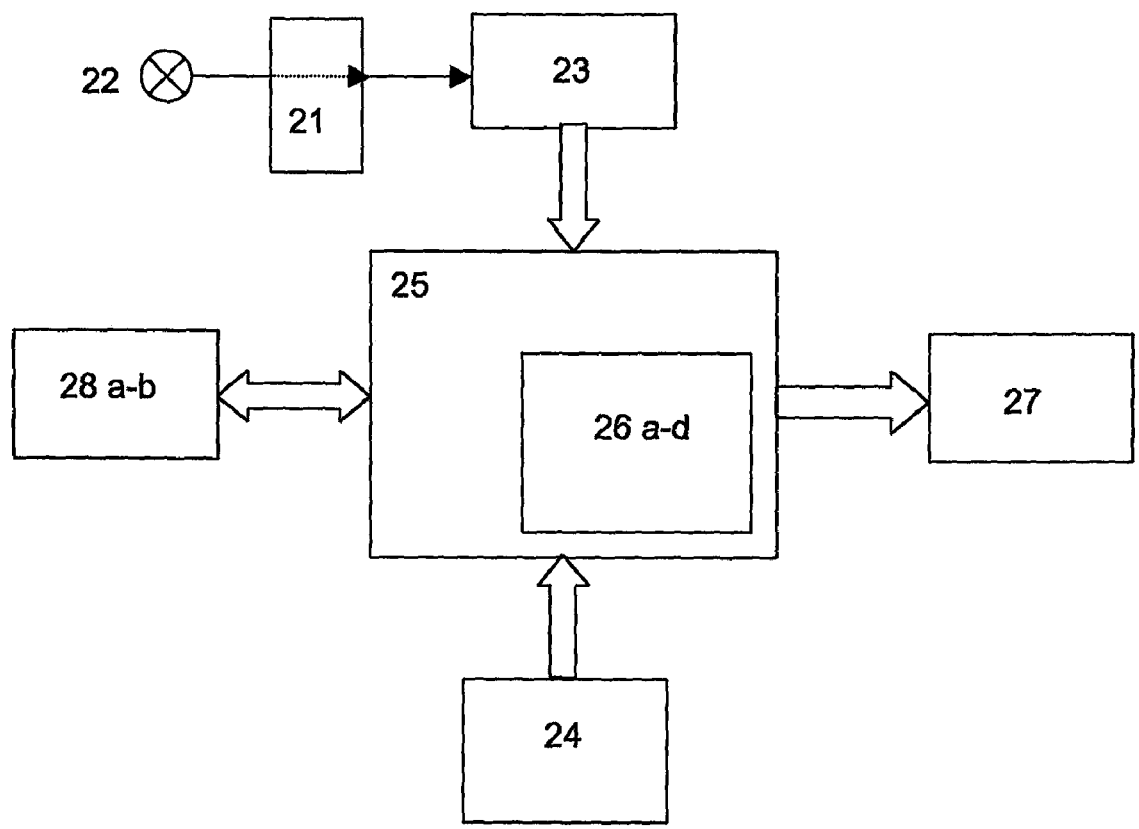

The present invention will be generally described from technical standpoint (theory, optics and information processing) in the following. Furthermore in connection to the enclosed drawings where FIG. 1 shows a handheld instrument FIG. 2 shows optic geometry, FIG. 3 shows the schematics for, signal processing and FIGS. 4 and 5 shows the correlation of HBX vs. reference measurements at an accredited laboratory.

In HBX a new way is chosen for the elimination of unwanted scattering effects, different from previous hemolysation or use of a big sensor for optimising incoming light. The blood is unaltered during the measurement. This is of importance since it is also possible to measure continuously in a blood stream without destroying and the measurement takes only a second. The problem of light scattering from the red cells effecting the measurement is solved through an optic-geometric design of the light conducting components and cuvette minimizing scattered light to reach the detector. Described more in detail below.

HBX is also based on a new combination of information searched, chosen light source, cuvette type, choice of spectrophotometer, measuring procedure, and signal handling optimised for the purpose and mathematical algorithms.

The invention comprises tree major parts, each one described below and in enclosed figures.

Optical Geometry

The solution of the scattering problem in the invention is based upon a fundamental theory for light scattering (reference Twersky, V. Absorption and multiple scattering by biological suspensions. J. Opt. Soc. Am. 60:1084-1093, 1970), in this case for fluids with suspended substance. The from theory emanating alternatives is determined by the actual conditions at the chosen optical/geometrical procedure. The design is correlated to the amount of scattered light to reach the detector of the photometer.

By arranging the light pathway to and from the cuvette using chosen angels of the light it is possible to prevent scattered light to reach the detector of the photometer or reduce the scattered light to a minimum and calculable level.

Optimal effect is reached by minimizing the measuring area to a size related to the size of the light pathway at the same time as the possible light deviation from said light pathway to and from the measuring object to the photometer is strongly limited. In principle this technique is designed to be contrary to the above mentioned USA method where a maximum of scattered light is collected for processing.

By choosing new fixed light sources with optimised characteristics e.g. light temperature, intensity (energy level) and adjustable exposure time or light sources with variable wave lengths it is possible to optimise the measuring set up for the spectrophotometer.

Basically two principles or alternatives are applicable in HBX; one is a broad band light source (white light) in connection to a spectrophotometer registration the light intensity as a function of wave length. The other alternative is a variable wave length mono chromatic light source of laser/maser in connection to a standard photometer registering absobrance/transmittant light intensity. Which alternative is chosen is determined by type of measuring object, situation and purpose.

The spectrophotometer in the first case is of type "monolithic multi-wavelengths diode-array, MMWDA" a new application (Hb-fractions) for this type of spectrophotometer for medical diagnostic purpose. The spectrophotometer is in this case combined with broad spectrum white light and measures the transmitting light from the light source at all wave lengths simultaneously.

The alternative combination is more like the previously existing standard methods with a simpler photometer in combination with a state of the art light source with variable frequency i.e. monochromatic light of different chosen wave lengths.

In prior art this was achieved by use of separate light sources, each with different wave length corrected by use of filters. In the alternative with MMWDA-photometer it is also possible but unnecessary to use a variable monochromatic light. Both combinations of light source and photometer separately makes it possible to directly measure and extract each of the searched haemoglobin fraction. This is one of the main characteristics of HBX which measures four different Hb-fractions The instrument is for the purpose equipped with reference values for all the actual Hb-fractions extinction curves. HBX admits the possibility to automatically present the value of each of the Hb-fractions and in addition the total Hb-value.

Signal Processing

Both of the above described alternatives light sources—photometer permits a great number of possible registrations of measuring data instantly, providing a possibility to choose freely the measuring points of interest from the complete measured sequences for further signal processing. Thereby the precision in the calculations can be decided and optimised.

The meted further admits calculation of the measuring error, for description of accuracy which is an integrated part of quality assurance.

The measurement is performed so quickly that no significant time for the measuring procedure needs to be taken into consideration. The complete analysis of all fractions is performed within a second which is unelectable in comparison with the other moments of an Hb-analysis e.g. sampling etc.

This further admits consecutive measurements over cycles of 30-60 per minute or even continues measurements.

Signal processing involves processor, memory for reference and measured data, algorithms for the chosen measuring data and compensation for possible scattering effects or deviations emanating from abnormal/unexpected data. The algorithm for calculation/elimination of light scattering is based upon accepted theories described in scientific publications. Further algorithms and approximations are based on least square method.

The invention HBX comprise several part inventions in terms of:

1) An optical geometry for minimizing scattered light to the detector in order to make measurements possible for accurate determination of chosen substances in colloid solutions, for example whole blood.
2) Two alternative measuring principles with the same purpose of creating data for selection of measuring points over a wide wave length range. This can be based upon a firm broad band white light source in combination with a spectrophotometer or a variable narrow wave lengths light source in combination with a standard type photometer.
3) A series of algorithms for signal processing designed for standard corrections, for the optical geometry and for calculations of approximations by use of a number of chosen measuring points.
4) A combination of above described part solutions enables very fast measuring cycles. The time consuming for each measuring cycle permits measurements faster than for example heart rate which makes the method suitable for continuous measuring of blood flow.

Even though HBX at every measuring situation enables a large amount of measuring data it not necessary to use all of these. In practise it is possible for a given purpose e.g. custom model/design of equipment, to utilize a limited or extended amount of data corresponding significantly to the purpose or application.

DETAILED DESCRIPTION

FIG. 1, shows a handheld HBX instrument. The area (3) with a dotted circle comprise of a light conductor of fibre type, cuvette, light trap etc. This area is emphasised in FIG. 2. showing the light path through cuvette and optical details. FIG. 3. shows the block schematics for units of logic, algorithms and the flow of measuring process. FIGS. 4 and 5 show two examples of actual measurements as regression analysis vs. reference laboratory method.

FIG. 1 shows that the instrument is designed with an optic light conductor with light source and photometer. In between a part for limitation of measuring area, a cuvette with the actual sample placed in a special holder (not visible in the drawing) a signal processing part, a display and a power supply/battery. Included in the signal processing part are in- and output, CPU, memory, program, various possible interfaces etc. The details are listed below with figures corresponding to FIGS. 1, 2, and 3.

1 Light source
2 Incoming light and direction of light towards the surface of the cuvette
3 Area for cuvette introduction (more alternative exists)
4 Cuvette cavity
5 Light conductor from the cuvette to the sensor (8)
6 Possible condenser and light collecting and focusing (lens) system
7 Possible aperture for incoming light to the cuvette
8 Photometer
9 Cuvette with measuring area (3)
10 Light "trap"
11 Control panel
12 Circuit board with CPU, memory, driver etc
13 Power supply, back up, net adapter, etc
14 Battery
15 Input and output, data, signal, alarm etc.
16 Card slot for PC
17 Place for extra memory card
18 Key board, display etc.
19 Cover
20 CPU, chips etc.
21 Cuvette holder with defined measuring area/zone/range?
22 Light source
23 Spectrophotometer of monolithic micro type
24 Memory unit med reference data e.g. "extinction coefficients" for actual Hb-fractions and chosen wave length spectra
25 Micro processor/Control Unit (CPU) for the various processes
26 $a$ algorithm for compensation of irregulariteties in the light source/white balance
26 $b$ algorithm for compensation of dark offset
26 $c$ algorithm for optimal approximation of chosen Hb-fractions, including background effects e.g. abnormal blood components and scattering to minimize the error of the measurement.
26 $d$ algorithm for calculation of total Hb from the measured components, including confidence interval/error for the measured values
27 display for reading of the measured/calculated values
28 $a$-$b$ Interface for input of identity information related to the test/sample e.g. patient and user ID, date, time etc. from source outside the system e.g., bar code reader via wire or wireless communication or LAN.
S Area for light conductor contact and light "trap"
T Main line—the optical axis, in the figure shown at 90 degrees angle vs. the cuvette surface.

The light from the light source (1) is applied exactly adapted and geometrically thorough as in FIG. 1. directly and possibly through correction with condenser and lenses (6), towards a diaphragm/aperture (7) or, as in FIG. 2. through an optic fibre (5) directly from the light source (1) to the measuring are of the cuvette (2) for incoming light at B. The optical fibre may have a diameter typical d2=0.1-3 mm.

The light angle of incidence is 90° (perpendicular) towards the cuvette surface and passes basically as a parallel pencil along the straight main light pathway, the optical axis A' towards F. In the case a laser/maser is used the light is in practice parallel to A'. The light source can be a LED, laser, flash etc. Light conducting may be used.

The light passes the cuvette walls and penetrates the sample The measuring cuvette is likely of micro stand type for distinct single measurements or a specially designed flow through type with a valve or a movable slot for continuous Hb-measurement in tubing.

The measuring cuvette is a container (9) in the size of one to a few square centimeters in which there are two close to parallel surfaces in the size of 5-20 mm2 and in between a cavity/slot—the sampling area—with a characteristic distance between the surfaces of 0.05-0.5 mm=slit distance.

The surfaces creates together a closed cavity where a small volume—defined as the slit or sampling volume—consists of a precise slit distance which is connected to the sample (e.g. blood) inlet. The cuvette is placed in a holder connected to the instrument. The holder ensures that the cuvette is brought in an exact position and geometry to the light conducting components and photometer.

The blood sample in the equivalent of a small drop is introduced in the sample cavity by the capillary force provided by the cuvette design. The shape and slit distance admits light transmission through a small but sufficient sampling volume for significant measuring of Hb-fractions by use of direct photometric method. Pencil light pathway through the sample along the optical axis is equal to the slit distance (t).

The cuvette including slit and other details is produced in one step with a precision that makes quality control in addition to the stipulated random sampling in the production redundant. This makes the cuvette inexpensive to produce.

A flow through cuvette for continuous measurement has channels/connections as inlet and outlet.

In the case of continuous measurement is based on consecutive/batch wise measurements there is a valve mechanism for pulsating supply of a specified blood volume. This volume can be typical 2-4 times the cuvette volume which for a normal flow through cuvette is in the range of 0.1-0.4 ml ($cm^3$). This provides a good flow through and rinsing of previous measurement. The device can be directly connected to the blood source e.g. the patient or research object who's blood pressure provides the flow.

As light passes through the sample fluid it will collide with particles e.g. blood cells. Some light will be absorbed and some will scatter and continue in different direction from the in falling. The intensity of the light is adjusted by the distance from the light source to the measuring area of the cuvette but also by adjusting is the aperture and electronic regulating by the control unit in the microprocessor. By immediate feedback, before and during measurement or transmission, of light variations in the light source, deviations can be immediately adjusted or calibrated automatically in the signal processing.

The light does not refract or diffract upon reaching the incoming transparent surface of the cuvette material containing the sample as (B and a-c) as in outgoing light surface (b-d) since the light in the configuration falls in at 90° perpendicular to the surface.

A certain part of the light finds it way through the blood within the volume a-b-c-d mainly parallel with the main line of light A'-F and continues parallel through the are A which is a light trap eliminating non parallel light. Collected light at e-f continues further through the light fibre F to the sensor (8).

Light is partly absorbed by Hb-fractions in the cells (suspended in the fluid/blood sample) and the remaining (transmitting) light continues unaltered along the main light line A-F.

Light hitting the suspension will be scattered in all directions and keeps hitting yet other suspended particles/cells where it will be absorbed or reflected according to known principles for light scattering in suspensions e.g. blood. The occurring scattered light will deviate in angle from the line A'-F. The geometry is designed in a way that the opening for outgoing light is small in comparison to the light path to the receiving light transmitter (fibre) leading to the sensor.

The behaviour pattern of the light depends on the wave length in relation to the aperture, the same as the receiving light conductor. Previously was mentioned that the receiving optical fibre has a diameter of 0.1-3 mm, corresponding to an area of $(0.1^2$ till $3^2) \times \pi/4 \approx 0.008-7$ mm2=size of the aperture for in and outgoing light preferably 1 mm2. The geometry limits the scattered light to enter the outgoing optical fibre and a very small part of the scattered light has such direction as to reach the sensor of the photometer. If the angle of incidence is larger than a certain value depending on the solution and refraction index of the cuvette, a total reflection will occur with no light reaching the sensor.

The outgoing light surface is directed towards the light conductor. A so called light "trap" (10) may be placed between the cuvette and the light conductor, with a space A which further reduces light non parallel (scattering). The light trap consists of a non reflective (light absorbing) space in the shape of a cylinder with a length L and an inner diameter ($d_2 < H < 30\ d_2$). The light tight ends of the cylinder has concentric holes of diameter $d_2$ for fitting to cuvette and light conductor. The transmitted light passes the light trap (10) before entering the light conductor where further deviated light will be absorbed in the cylinder A. The length is in relation to the diameter of the light conductor and can be typical between 5-30× the diameter $d_2$ or in the case of a diameter $d_2$=0.1 mm between 0.5-3 mm. Possible scattered light which fits within the boundaries of the geometry can be considered as parallel when reaching the sensor, correction can be made in the signal processing.

The electronic parts of the instrument contains details for monitoring and signal processing with different choices of manual or pre-chosen automatic functions/modes. It contains CPU, memory, programs, algorithms, time oscillator, drivers, display, interface to external units, input for external units e.g. bar code readers. It has mains power supply, battery back up etc. Communication with LAN and Internet, using current standards of interface e.g. infra light, Blue Tooth etc.

The electronic part is built mainly of standard components like processors, memories, and drivers. The specific signal processing is programmed in the processor along with factors concerning blood components and/or other in the sample intended components.

Corrections and calculations of approximations is performed in a number of internal developed algorithms which typical can be four or more. These are programmed in the processor for signal processing. FIG. 3 with figure references.

The described configuration of units and signal processing with different algorithms and its purpose is one appropriate variant depending the choice of components, purpose and object of measuring, measuring situation, optical geometry etc. Other configurations may be considered including additional or fewer algorithms to measuring result. In certain applications the measuring points may also be additional or fewer. The presentation of the measuring results can be varied and selected depending on the main interest of the user e.g. Hb-fractions or simple total Hb. In some applications it is of value to follow a time dependent picture (profile) the values must then be stored in a time related way for retrospective analysis. Different levels of automation may be included to facilitate for the operator.

The picture of the signal registered by the photometer will be corrected and compensated for by stepwise calculations— the algorithm process—for deviations emanating from geometry, light variations and fluctuations, back ground influence, light scattering, absorption by other components than the desired Hb-fractions etc. The signal processing executes at the operators command or automatically a suitable number of measuring points from a registered measuring picture. Based upon the chosen measuring points a series of iterations is automatically performed according to "the least square method" for optimal fit of measuring values compared to stored reference values e.g. —fractions.

This corresponds to the direct results/Hb-values—as fractions or as total—which is coded and stored to avoid mix-up. The values are shown on a display and may by the instrument be transmitted by wire or wireless to central data base. The whole process is basically instant or within a second without delay.

The number of measuring points to obtain desired accuracy of the result can be determined automatically at operators choice. A minimum of two points may give enough accuracy for certain purposes. Up to seven measuring points is used today In HBX an optional number of measuring points can be chosen (2<measuring points<100) but the net contribution of each measuring point is diminished over a certain numbers (provided the optimal ones are used).

FIG. 4 and FIG. 5 shows two examples from a variety of laboratory test comparisons of HBX HBX-method vs. the excising reference meted (ABL) performed at the accredited Hospital Clin. Chem. Laboratory at Helsingborg Hospital. The result is presented as analysis of regression.

FIG. 4 shows the HB-fraction—oxygenised haemoglobin (HbO2)—one essential component of CO-Oximetry measurements. HbO2 is normally the dominating Hb-fraction and in intensive care the most important. Depending on the specific situation of the patient and purpose of the Hb-measurement, other components may be the most important. As shown in the diagram the correlation is 0.99 which is very high.

FIG. 5 shows a regression analysis of HBX vs. reference method for total Hb, the sum of the different Hb-fractions. Total Hb is the most frequent Hb measurement in health care and blood banking. As shown in the diagram the correlation is 0.98. This is considered as high with low deviations and in line with current methods and criteria for Hb measurement.

The results shown in FIGS. 4 and 5 verifies that the ideas, theory and inventions behind the HBX concept concerning the combination of the specific choices and design of "optical geometry" and light source—detector in combination with HBX signal processing is realistic and applicable in practice.

The invention claimed is:

1. A device for determination of selected properties of a liquid medium comprising:
   a light source for providing light through a sample of the liquid medium;
   a holder for carrying a container with the sample of the liquid medium;
   a light trap arranged for reducing the amount of scattered light in the light having passed through the sample of the liquid medium;
   a light receiving unit for detecting the light having passed through the sample of the liquid medium and the light trap; and
   a processor for determining at least one selected property of the liquid medium based on the light detected by the light receiving unit.

2. The device according to claim 1, wherein the light trap is arranged between the holder and the light receiving unit for preventing scattered light exiting the sample of the liquid medium from reaching the light receiving unit.

3. The device according to claim 1, wherein the light trap is designed as a cylinder of light absorbing material having concentrically placed entry and exit holes of a diameter smaller than an inner diameter of the cylinder.

4. The device according to claim 3, wherein a length of the cylinder is 5 to 30 times the diameter of the entry and exit holes.

5. The device according to claim 1, wherein the light source is a broad band light source of white light and the light receiving unit is arranged for registering intensity of light having passed through the sample of the liquid medium and the light trap as a function of wave length or frequency of the light.

6. The device according to claim 5, wherein the light receiving unit is a spectrophotometer of monolithic multi-wavelengths diode-array type.

7. The device according to claim 1, wherein the light source is a variable wave length monochromatic light source and the light receiving unit is arranged for registering intensity of light having passed through the sample of the liquid medium and the light trap.

8. The device according to claim 1, further comprising a light conducting device arranged between the light source and the container, when placed in the holder, for directing light from the light source to a measuring area opening of the container.

9. The device according to claim 8, wherein the light conducting device is designed so that the light forwarded from the light source has an angle of incidence of 90° relative the measuring area opening.

10. The device according to claim 8, wherein the measuring area opening has the same geometrical shape and cross section area as the light exiting the light conducting device.

11. The device according to claim 1, further comprising a lens system arranged between the light source and the container, when placed in the holder, for focusing light from the light source into a parallel beam having an angle of incidence of 90° relative a measuring area opening of the container.

12. The device according to claim 1, further comprising a light conducting device arranged between the light trap and the light receiving unit for forwarding, to the light receiving unit, light perpendicular to a measuring area opening of the container and having passed through the light trap.

13. The device according to claim 12, wherein the light conducing device has a cross section area of a same shape and geometrical size as the measuring area opening of the container.

14. The device according to claim 1, wherein the liquid medium is whole blood.

15. The device according to claim 1, wherein the processor is arranged for determining the concentration of at least one substance in the liquid medium based on the light detected by the light receiving unit.

16. The device according to claim 15, wherein the processor is arranged for determining at least one of total haemoglobin or at least one haemoglobin fraction in the sample of the liquid medium based on the light detected by the light receiving unit.

17. The device according to claim 15, wherein the processor is arranged for determining multiple haemoglobin fractions in the sample of the liquid medium based on the light detected by the light receiving unit.

18. The device according to claim 1, further comprising:
   a flow inlet channel connected to the container for providing the liquid medium to a measuring area of the container; and
   a flow outlet channel connected to the container for providing an outlet of the liquid medium from the measuring area.

19. A method for determination of selected properties of a liquid medium comprising:
   guiding light from a light source to a container comprising a sample of the liquid medium;
   reducing the amount of scattered light in the light having passed through the sample of the liquid medium;
   guiding the non-scattering light having passed through the sample of the liquid medium to a light receiving unit; and
   determining a selected property of the liquid medium based on the light detected by the light receiving unit.

* * * * *